(12) United States Patent
Van Wijck

(10) Patent No.: US 6,245,909 B1
(45) Date of Patent: Jun. 12, 2001

(54) METHOD FOR THE PREPARATION OF MELAMINE

(75) Inventor: Julius G. T. Van Wijck, Maastricht (NL)

(73) Assignee: DSM NV, Geleen (NL)

( * ) Notice: Subject to any disclaimer, the term of this patent is extended or adjusted under 35 U.S.C. 154(b) by 0 days.

(21) Appl. No.: 09/210,645

(22) Filed: Dec. 14, 1998

Related U.S. Application Data

(63) Continuation of application No. PCT/NL97/00333, filed on Jun. 11, 1997.

(30) Foreign Application Priority Data

Jun. 13, 1996 (NL) .................................................... 1003328

(51) Int. Cl.⁷ ........................ C07D 251/60; C07D 251/62
(52) U.S. Cl. ............................................................. 544/201
(58) Field of Search ............................................. 544/201

(56) References Cited

U.S. PATENT DOCUMENTS

| 3,166,294 | 1/1965 | Middler ................................. 544/201 |
| 4,565,867 | 1/1986 | Thomas et al. ....................... 544/201 |
| 5,514,796 | 5/1996 | Best et al. ............................. 544/201 |
| 5,514,797 | * 5/1996 | Best et al. ............................. 544/201 |
| 5,721,363 | * 2/1998 | Canzi et al. .......................... 544/201 |

FOREIGN PATENT DOCUMENTS

| 747 366 | 12/1996 | (EP) . |
| 96 20182 | * 7/1996 | (WO) . |
| 96 20183 | * 7/1996 | (WO) . |
| 96/20182 | 7/1996 | (WO) . |
| 96/20183 | 7/1996 | (WO) . |
| 96/23778 | 8/1996 | (WO) . |

\* cited by examiner

*Primary Examiner*—Richard L. Raymond
*Assistant Examiner*—Venkataraman Balasubramanian
(74) *Attorney, Agent, or Firm*—Pillsbury Winthrop LLP

(57) ABSTRACT

The invention relates to a method for the preparation of melamine from urea via a high-pressure process in which solid melamine is obtained by transferring the melamine melt leaving the melamine reactor to a cooling vessel where the melamine melt is cooled by means of liquid ammonia. The melamine melt is cooled to a temperature of between about 50° C. and about 350° C. by means of liquid ammonia, a mixture comprising ammonia and melamine being formed, after which all or part of this mixture is transferred to an expansion vessel, the composition being contacted with ammonia for about one minute to about five hours, following which solid melamine is liberated from the composition.

9 Claims, 1 Drawing Sheet

METHOD FOR THE PREPARATION OF MELAMINE

Figure 1:
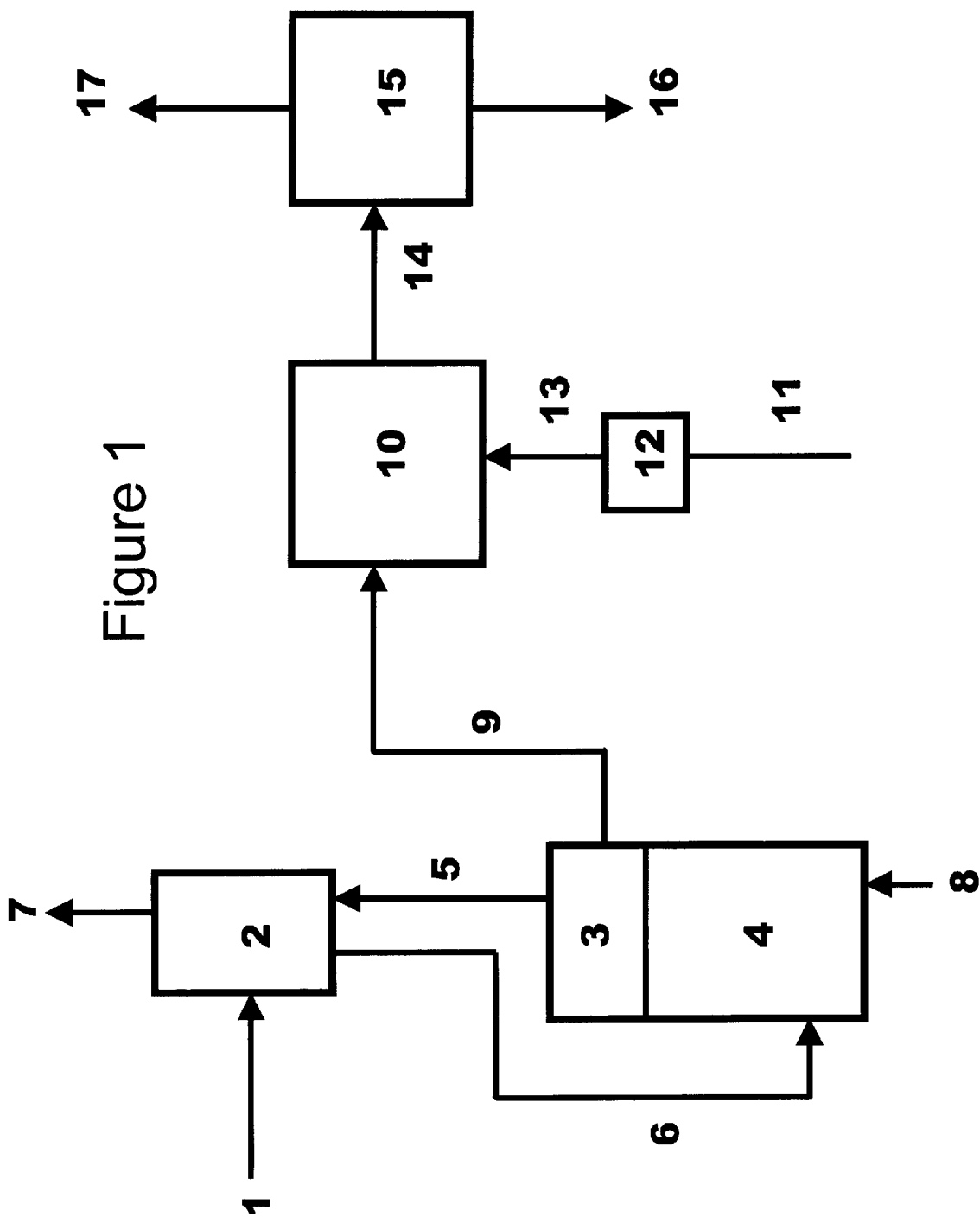

This is a Continuation of International Appln. No. PCT/NL97/003338 filed Jun. 11, 1997 which designated the U.S.

1. Field of the Invention

The invention relates to a method for the preparation of solid melamine using a high-pressure process in which the melamine melt is transferred from the reactor to a vessel and is cooled using liquid ammonia so as to obtain melamine having a very high degree of purity (99.5 wt % to 99.95 wt %) as a dry powder directly from the reactor product.

2. Description of the Prior Art

Melamine (2,4,6-triaminosymtriazine) is a white crystalline product obtained by heating urea.

Purified crystalline melamine can be combined with formaldehyde to form melamine resin. Characteristics of subsequent products formed from the melamine resin are critically dependent upon the level of purity of the crystalline melamine used to form the resin. Obtaining crystalline melamine of very high purity is therefore an essential first step to melamine related product formulation.

The first step in melamine resin formation from crystalline melamine is the production of trimethylol melamine. This molecule can combine further with others of the same kind by a condensation reaction. Excess formaldehyde or melamine can also react with trimethyol melamine or its polymers, providing many possibilities of chain growth and cross-linking. The nature and degree of polymerization can be varied by pH and the degree of heat applied in the curing process. Impurities in the melamine also effect the nature of the polymerization reaction.

A major advantage of melamine resins is that they are more water resistant and heat resistant than urea resins. Melamine resins may be water-soluble syrups (low molecular weight) or insoluble powders (high molecular weight) dispersible in water. Melamine resins are widely used as molding compounds with α-cellulose, wood flour, or mineral powders as fillers and with coloring materials. Melamine resins are also used in laminating, producing boil-proof adhesives, increasing the wet strength of paper, textile treatment, leather processing, and producing dinnerware and decorative plastic items. The use of melamine resins in general results in superior products over urea resin products.

Butylated melamine resins are formed by incorporating butyl or other alcohols during resin formation. These resins are soluble in paint and enamel solvents and in other surface coatings, often in combination with alkyds. They give exceptional curing speed, hardness, wear resistance, and resistance to solvents, soaps and foods.

Melamine-acrylic resins are water soluble and are used for formation of water-base industrial and automotive finishes. The use of melamine-acrylic resins provides smooth, durable surface finishes. However, as is the case with other melamine-based products, the superiority of melamine-acrylic resin products is related to the high level of purity of the initial crystalline melamine product.

A method of purification of the initial melamine product is achieved by recrystallization from water to obtain a highly pure melamine product (99 wt %). One method of obtaining and purifying melamine is described in U.S. Pat. No. 4,565,867 issued to Thomas et al., the complete disclosure of which is incorporated herein by reference. The Thomas reference discloses a high-pressure process for the preparation of melamine from urea. In particular, the pyrolysis of urea in a reactor at a pressure of about 10.3 MPa to about 17.8 MPa and a temperature of about 354° C. to about 427° C. for producing a reactor product is described.

This reactor product contains liquid melamine, $CO_2$ and $NH_3$ and is transferred under pressure, as a mixed stream, to a separator. In this separator, which is kept at virtually the same pressure and temperature as the reactor, the reactor product is separated into a gaseous stream and a liquid stream. The gaseous stream contains $CO_2$ and $NH_3$ off-gases and also melamine vapour. The liquid stream substantially consists of liquid melamine. The gaseous stream product and the liquid stream product are treated differently. The gaseous product is transferred to a scrubber unit, while the liquid melamine is transferred to a product cooler. In the scrubber unit the above-mentioned $CO_2$ and $NH_3$ off-gases, which contain melamine vapour, are scrubbed, at virtually the same pressure as the reactor pressure, with molten urea so as to pre-heat the urea and cool said off-gases and remove the melamine that is present from the off-gases. The pre-heated molten urea, which contains melamine, is then fed to the reactor. In the product cooler the liquid melamine is reduced in pressure and cooled by means of a liquid cooling medium (preferably liquid ammonia) so as to produce a solid melamine product without washing or further purification.

The disadvantage of the above-mentioned Thomas method is that melamine having a purity of only approximately 99 wt % is obtained. Thomas teaches a theoretical conversion yielding only 99.19 wt % pure melamine. However, the example provided by the Thomas reference at column 9, line 61 through column 10, line 2, shows the Thomas method obtaining melamine with an even lower purity of only 98.0 wt %. In the Thomas example, the melamine product remains 0.81 wt % urea, 0.03 wt % $CO_2$, 0.05 wt % melamine-related compounds and 0.07 wt % organic solids (melem, melam, and other solids) are present. Such a product is not pure enough for universal application and especially not pure enough for application in coatings. Besides that the storage stability of the product is insufficient and as a result of this the properties of the product deteriorates.

A need therefore exists to provide an economical method to obtain highly purified melamine (99.5 wt % to 99.95 wt %).

3. SUMMARY OF THE INVENTION

An object of the present invention is to obtain an improved process for the preparation of melamine from urea in which melamine having a high degree of purity is obtained as a dry powder directly from the reactor product. More particularly it is an object of the present invention to obtain an improved high-pressure process for the preparation of melamine from urea in which melamine having a high degree of purity is obtained as a dry powder directly from the liquid melamine melt through cooling.

The present invention provides a method of preparation of highly purified solid melamine from urea melt obtained from a urea plant, the method comprising the combination of steps of:

(1) providing urea melt to a scrubber unit;
(2) transferring the urea melt from the scrubber unit to a melamine reactor;
(3) heating the urea melt in the melamine reactor to a temperature and pressure sufficient to produce a melamine melt and off-gases, the melamine melt being a composition comprising liquid melamine, melamine by-products and the off-gases being a mixture comprising $CO_2$, $NH_3$ and melamine vapor;

(4) exhausting the off-gases to the scrubber unit where the urea melt in the scrubber unit washes the melamine vapor out of the off-gases to form recovered liquid melamine, the off-gases then being exhausted out of the scrubber unit for recyling to a urea plant and the recovered liquid melamine being returned to the melamine reactor;

(5) transferring the melamine melt to a cooling vessel;

(6) exposing the melamine in the cooling vessel to ammonia for a period of time sufficient to convert the melamine by-products to melamine.

The present invention provides a first alternative method of preparation of highly purified solid melamine from urea melt obtained from a urea plant, the method comprising the combination of steps of:

(1) providing urea melt to a scrubber unit;

(2) transferring the urea melt from the scrubber unit to a melamine reactor;

(3) heating the urea melt in the melamine reactor to a temperature and pressure sufficient to produce a melamine melt and off-gases, the melamine melt being a composition comprising liquid melamine, melamine by-products and the off-gases being a mixture comprising $CO_2$, $NH_3$ and melamine vapor;

(4) exhausting the off-gases to the scrubber unit where the urea melt in the scrubber unit washes the melamine vapor out of the off-gases to form recovered liquid melamine, the off-gases then being exhausted out of the scrubber unit for recyling to a urea plant and the recovered liquid melamine being returned to the melamine reactor;

(5) transferring the melamine melt to a cooling vessel;

(6) exposing the melamine in the cooling vessel to ammonia for a period of time sufficient to convert the melamine by-products to melamine; and (7) transferring the melamine to a vessel and recovering the melamine by lowering the pressure in the vessel to atmospheric pressure leaving a product of highly pure solid melamine.

The present invention provides a second alternative method of preparation of highly purified solid melamine from urea melt obtained from a urea plant, the method comprising the combination of steps of:

(1) providing urea melt to a scrubber unit;

(2) transferring the urea melt from the scrubber unit to a melamine reactor;

(3) heating the urea melt in the melamine reactor to a temperature and pressure sufficient to produce a melamine melt and off-gases, the melamine melt being a composition comprising liquid melamine, melamine by-products and the off-gases being a mixture comprising $CO_2$, $NH_3$ and melamine vapor;

(4) exhausting the off-gases to the scrubber unit where the urea melt in the scrubber unit washes the melamine vapor out of the off-gases to form recovered liquid melamine, the off-gases then being exhausted out of the scrubber unit for recyling to a urea plant and the recovered liquid melamine being returned to the melamine reactor;

(5) transferring the melamine melt from the melamine reactor to an aging vessel, the aging vessel being at the same temperature and pressure as the scrubber unit;

(6) exposing the melamine melt in the aging vessel to a mixture comprising ammonia and melamine for a period of time;

(7) transferring the melamine melt to a cooling vessel;

(8) exposing the melamine melt in the cooling vessel to ammonia for a period of time sufficient to convert the melamine by-products to melamine; and (9) transferring the melamine to a vessel and recovering the melamine by lowering the pressure in the vessel to atmospheric pressure leaving a product of highly pure solid melamine.

4. DETAILED DESCRIPTION OF THE INVENTION

Applicant has discovered that the purity of the melamine can be increased and the storage stability can be improved substantially over conventional processes for producing solid melamine from urea (preferrably) using a method comprising a combination of steps.

The method of the invention is achieved a plant suitable for the preparation of melamine from urea. A plant suitable for the preparation of melamine can comprise a scrubber unit, a melamine reactor integrally combined with a gas/liquid separator or optionally connected to a distinct gas/liquid separator, a cooling vessel and an expansion vessel.

Each of the vessel used in the process are capable of containing pressurized fluids and are connected by lines through which the transfer of materials can be by gravity force or may be augmented by mechanical pumping devices. A plant suitable for being adapted or retrofitted to permit practice of the present invention is described in the Thomas reference, the complete disclosure of which is incorporated herein by reference.

The scrubber unit comprises a vessel comprising at least one access for urea melt input, at least one line access for melamine melt and off-gases input, at least one line outlet for urea melt discharge, and at least one line outlet for $CO_2$, $NH_3$ gases discharge. The scrubber unit may be provided with a jacket so as to provide extra cooling in the scrubber unit. The scrubber unit may also be provided with internal cooling bodies or baffels.

The melamine reactor comprises a vessel comprising at least one line access for a mixture comprising urea melt and liquid melamine input, at least one line access for ammonia or the like, at least one line outlet to an integral gas/liquid separator (optionally a distinct gas/liquid separator), and at least one line outlet for a mixture comprising melamine melt to be transferred to the cooling vessel. The integral gas/liquid separator or optionally, the distinct gas/liquid separator, will comprise a vessel comprising at least one line access from the melamine reactor and at least one line outlet to the scrubber unit.

The cooling vessel comprises at least one line access for a mixture comprising melamine melt, at least one line access from a pump providing a cooling fluid, for example liquid ammonia or the like, and at least one line outlet to an expansion vessel.

The expansion vessel comprises at least one line access for a mixture comprising liquid melamine from the cooling vessel, at least one line outlet excess ammonia, and at least one outlet for solid melamine product.

The reaction of the invention which provides highly purified solid melamine from urea also produces by products of $NH_3$ and $CO_2$. The reaction proceeds according to the following reaction equation:

The first step in the production of melamine is to pump urea melt from a urea plant into a scrubber unit. The urea melt is provided to the scrubber unit at a pressure of about 5 MPa to about 25 MPa, preferably about 8 MPa to about 20 MPa, and at a temperature above the melting point of urea.

In the scrubber unit the urea melt comes into contact with the reaction gases from the melamine reactor combined with a gas/liquid separator or from a distinct gas/liquid separator installed downstream of the reactor. In the case of a separate gas/liquid separator, the pressure and temperature are virtually the same as the temperature and pressure in the melamine reactor. The reaction gases substantially consist of $CO_2$ and $NH_3$ and also contain an amount of melamine vapour. The urea melt washes the melamine vapour out of the off-gas and carries this liquid melamine back to the reactor. In the scrubbing process the off-gases are cooled from the higher temperature of the melamine reactor, for example, from the range of about 350° C. to about 425° C. in the melamine reactor, to a range of about 170° C. to about 240° C. in the scrubber unit, the urea melt being heated to about 170° C. to about 240° C. The off-gases are removed from the top of the scrubber unit and for instance returned to a urea plant for use as a starting material for the production of urea.

The urea melt is withdrawn from the scrubber unit together with the washed-out liquid melamine and transferred, for instance via a high-pressure pump, to the melamine reactor, which has a pressure of about 5 MPa to about 25 MPa, and preferably of about 8 MPa to about 20 MPa. Use can also be made of gravity for transferring the urea melt to the melamine reactor by placing the scrubber unit above the reactor.

In the melamine reactor the molten urea is heated to a temperature of about 325° C. to about 450° C., preferably of about 350° C. to about 425° C., at a pressure as described above, under which conditions the urea melt is converted into liquid melamine, $CO_2$ and $NH_3$. An amount of ammonia, for instance, as a liquid or hot vapor, can be metered to the reactor. The ammonia supplied can serve to prevent the formation of melamine condensation products such as melam, melem and melon, as well as promote mixing in the reactor. The amount of ammonia fed to the melamine reactor is about 0 mol to about 10 mol per mol urea; preferably, about 0 mol to about 5 mol ammonia is used, and in particular about 0 mol to about 2 mol ammonia per mol urea.

The $CO_2$ and $NH_3$ formed in the reaction as well as the extra ammonia supplied collect in the gas/liquid separator, for instance in the top of the melamine reactor, but optionally a distinct gas/liquid separator downstream of the reactor can be provided. The gas/liquid separator serves to separate the off-gases from the liquid melamine.

The resulting off-gas mixture is sent to the scrubber unit for recovery of melamine liquid from melamine vapour and for preheating of the urea melt. The liquid melamine is withdrawn from the reactor and transferred to a cooling vessel.

In the cooling vessel the liquid melamine melt is cooled, by evaporation of ammonia, to a temperature between about 50° C. and about 350° C., preferably between about 75° C. and about 275° C., and in particular between about 100° C. and about 200° C. The pressure in the cooling vessel is preferably>about 2 MPa and in particular between about 8 MPa and about 25 MPa. The resulting mixture comprising melamine and ammonia is then transferred to an expansion vessel. It is also possible to transfer just the melamine to the expansion vessel and to add additional ammonia. The mixture comprising melamine and ammonia is held in the expansion vessel for a period of time at the same temperatures and pressures as exist in the cooling vessel.

In the expansion vessel, before the composition is expanded, the temperature and pressure are preferably about the same as the pressure and the temperature in the cooling vessel. In the expansion vessel the composition consisting of melamine and ammonia is kept in contact with each other for a period of time. The residence time of the mixture comprising melamine and ammonia in the expansion vessel is about one minute to about five hours, after which the mixture is expanded. The purified solid melamine is recovered from the expansion vessel and the ammonia is recirculated and reintroduced into the process.

In another embodiment of the method the liquid melamine, before being transferred to the cooling vessel, is treated in an aging vessel. In the aging vessel the liquid melamine can again be contacted with about 0.01 mol to about 10 mol ammonia per mol melamine and preferably with about 0.1 mol to about 2 mol ammonia per mol melamine. The contact time in the aging vessel is between about one minute and about three hours, preferably between about two minutes and about two hours. The temperature in the aging vessel is between about 325° C. and about 450° C. and the pressure between about 5 MPa and about 25 MPa. Preferably, the temperature and pressure in the aging vessel are virtually the same as in the reactor where urea is converted into melamine. The ammonia leaving the aging vessel can subsequently be passed to the melamine reactor. In the aging vessel among other things the melamine condensation products are converted into melamine. The location of the aging vessel is downstream of the reactor/separator.

In yet another embodiment there is an extra evaporation step between the melamine reactor and cooling vessel. In this embodiment gaseous melamine is cooled by means of liquid ammonia.

The invention will be demonstrated with reference to FIG. 1, which schematically represents the melamine preparation.

In this FIGURE, urea melt having a temperature of about 140° C. is fed through line 1 to scrubber unit 2. From the gas/liquid separator 3, which is combined with melamine reactor 4, a gas stream consisting of $NH_3$, $CO_2$ and melamine vapour is fed to scrubber unit 2 via line 5. In this scrubber unit 2 the melamine is washed out of the gas stream by means of the urea melt. Via line 6 the urea melt, together with the washed-out liquid melamine, is transferred from the scrubber unit 2 to the melamine reactor 4. The gas stream containing $NH_3$ and $CO_2$ leaves the scrubber unit 2 via line 7 to go to, for instance, an adjoining urea plant. Extra ammonia can be provided through line 8 to melamine reactor 4, for instance to suppress byproduct formation. The reaction in the melamine reactor 4 can be carried out at a high pressure, preferably between about 5 MPa and about 25 MPa, without the presence of a catalyst. The temperature of the reaction varies between about 325° C. and about 450° C. and is preferably between about 350° C. and about 425° C. The liquid stream from gas/liquid separator 3 is passed via line 9 to cooling vessel 10. Ammonia is provided through line 11 to pump 12 and then pumped through line 13 at the desired pressure and temperature to cooling vessel 10. In the cooling vessel 10 the melamine melt is cooled by means of ammonia to a temperature between about 50° C. and about 350° C., preferably between about 75° C. and about 275° C., and in particular between about 100° C. and about 200° C. The pressure in the cooling vessel 10 is preferably greater than about 2 MPa and in particular the pressure is between about 8 MPa and about 25 MPa. This cooling step results in a mixture comprising melamine and ammonia. Part or all of this ammonia and melamine mixture is then transferred to the expansion vessel 15. Preferably, the melamine alone is transferred from the cooling vessel 10 to the expansion vessel 15. Alternatively, part or all of the ammonia from the mixture can be transferred with the melamine to the expansion vessel 15. If only the melamine is transferred, additional ammonia can be metered to the expansion vessel 15. In the expansion vessel 15, the mixture of melamine and ammonia or, in the alternative, the melamine and the additionally added ammonia are allowed to remain in contact with each other for one minute to five hours, preferably for between ten minutes and two hours. During this contact period in the expansion vessel 15 the temperature and pressure in the expansion vessel 15 is substantially the same as the temperature and pressure in the cooling vessel 10. It is also possible to use an intermediate contact vessel between the cooling vessel 10 and the expansion vessel 15 in which the melamine mixture is maintained in contact with ammonia for a period of time similar to the period of time in which the mixture is held in contact in the expansion vessel 15. The contact time between the melamine and the ammonia is essential to permit the condensation products of melamine such as melam, melem and melon to be converted into solid melamine, thereby providing increased purity of the solid melamine product. Finally, the mixture in the expansion vessel is expanded to virtually atmospheric pressure, the highly purified solid melamine product being discharged via line 16. The ammonia obtained from the expansion vessel is returned to the process via line 17.

The embodiments as presented in the FIGURE and described in the above description can also be provided with a distinct separator unit 3 instead of a combined melamine reactor/separator unit 3,4. The embodiments can also include an aging vessel to receive the liquid melamine immediately after leaving the melamine reactor enroute via line 9 to the cooling vessel 10. The invention may also include an evaporator downstream of the melamine reactor/separator in line 9 just prior to the cooling vessel.

EXAMPLE

From a melamine reactor 100 g of melamine melt was transferred to an autoclave and there combined with ammonia. A mixture of powdery melamine and ammonia was formed. The autoclave contents were kept at a pressure of 8 MPa and a temperature of 175° C. The residence time in the autoclave was 45 minutes, after which the mixture was expanded to atmospheric pressure. Melamine powder having a purity of 99.7 wt. % was obtained.

The advantage of the method according to the present invention is that melamine having a very high degree of purity (99.5 wt % to 99.95 wt %), useful in virtually all applications, especially coatings, is obtained as a dry powder directly from the reactor.

What is claimed is:

1. A method of preparation of highly purified solid melamine from urea melt obtained from a urea plant, the method comprising the combination of steps of:

(1) providing urea melt to a scrubber unit;

(2) transferring said urea melt from said scrubber unit to a melamine reactor;

(3) heating and pressurizing said urea melt in said melamine reactor to a temperature and a pressure sufficient to produce a melamine melt and off-gases, said melamine melt comprising liquid melamine, melamine by-products and the off-gases comprising $CO_2$, $NH_3$ and melamine vapor;

(4) exhausting said off-gases to said scrubber unit where said urea melt washes said melamine vapor out of said off-gases to form recovered liquid melamine, said off-gases then being exhausted out of the scrubber unit and said recovered liquid melamine being returned to said melamine reactor;

(5) transferring said liquid melamine to a cooling vessel and cooling said liquid melamine melt therein under pressure to form solid melamine, by evaporation of ammonia, to a temperature between about 50° C. and about 350° C.;

(6) transferring said solid melamine to an expansion vessel;

(7) holding said solid melamine in said expansion vessel under ammonia pressure for a residence time, the residence time being between about ten minutes to about five hours;

(8) reducing the pressure in said expansion vessel to atmospheric pressure; and (9) recovering highly pure solid melamine.

2. The method according to claim 1 wherein said melamine is cooled to a temperature of between 75° C. and 275° C.

3. The method according to claim 1 wherein said melamine is cooled to a temperature of between 100° C. and 200° C.

4. The method according to claim 1 wherein said melamine is contacted with ammonia in said expansion vessel for ten minutes to two hours.

5. The method according to claim 1 wherein substantially only said melamine is transferred from said cooling vessel to the expansion vessel.

6. The method according to claim 1 wherein said pressure in said cooling vessel during said step of cooling said melamine melt is higher than 2 MPa.

7. A method of preparation of highly purified solid melamine from urea melt obtained from a urea plant, the method comprising the combination of steps of:

(1) providing urea melt to a scrubber unit;

(2) transferring said urea melt from said scrubber unit to a melamine reactor;

(3) heating and pressurizing said urea melt in said melamine reactor to a temperature and a pressure sufficient to produce a melamine melt and off-gases, said melamine melt comprising liquid melamine, melamine by-products and the off-gases comprising $CO_2$, $NH_3$ and melamine vapor;

(4) exhausting said off-gases to said scrubber unit were said urea melt washes said melamine vapor out of said off-gases to form recovered liquid melamine, said off-gases then being exhausted out of the scrubber unit and said liquid melamine being returned to said melamine reactor;

(5) transferring said liquid melamine to an aging vessel; said aging vessel containing said liquid melamine and ammonia for two minutes to two hours;

(5) transferring said liquid melamine to a cooling vessel, wherein the liquid melamine melt is cooled, by evaporation of ammonia, to a temperature between about 50° C. and about 350° C.

8. A method for preparing highly pure solid melamine from urea melt, the method comprising, in numerical sequence, the steps of:

(1) providing urea melt to a scrubber unit;

(2) transferring said urea melt from said scrubber unit to a melamine reactor;

(3) heating and pressurizing said urea melt in said melamine reactor to a temperature and a pressure sufficient to produce a melamine melt and off-gases, said melamine melt comprising liquid melamine, melamine by-products, said off-gases comprising $CO_2$, $NH_3$, and melamine vapor;

(4) removing said off-gases from said melamine reactor and passing said off-gases through said scrubber unit wherein said urea melt washes said melamine vapor out of said off-gases to form recovered liquid melamine, the remainder of said off-gases then being removed from said scrubber unit and said recovered liquid melamine being returned to said melamine reactor with said urea melt;

(5) transferring said liquid melamine to a cooling vessel, wherein the liquid melamine melt is cooled by contact with and evaporation of liquid ammonia to form solid melamine having a temperature of not more than 175° C. under an ammonia pressure of at least 5 MPa;

(6) transferring said solid melamine to an expansion vessel;

(7) holding said solid melamine in said expansion vessel under ammonia pressure approximately equal to the pressure of said cooling vessel for a residence time, the residence being at least ten minutes;

(8) reducing the pressure in said expansion vessel to atmospheric pressure; and (9) recovering highly pure solid melamine.

9. The method according to claim 8, wherein the method further comprises the additional step:

(4a) transferring said liquid melamine to an aging vessel and aging said liquid melamine for a predetermined aging period in an ammonia atmosphere at a temperature above the melting point of melamine and under pressure, said pressure being at least 5 MPa and said aging period being at least two minutes;

said aging step being completed before said step of transferring said melamine to said cooling vessel.

* * * * *